United States Patent
Bogatu et al.

(10) Patent No.: US 12,408,876 B2
(45) Date of Patent: Sep. 9, 2025

(54) METHOD AND APPARATUS FOR ESTIMATING THE RELIABILITY OF CARDIAC OUTPUT MEASUREMENTS

(71) Applicant: KONINKLIJKE PHILIPS N.V., Eindhoven (NL)

(72) Inventors: Laura Ioana Bogatu, Eindhoven (NL); Jens Muehlsteff, Aachen (DE)

(73) Assignee: KONINKLIJKE PHILIPS N.V., Eindhovent (NL)

( * ) Notice: Subject to any disclaimer, the term of this patent is extended or adjusted under 35 U.S.C. 154(b) by 298 days.

(21) Appl. No.: 18/024,392

(22) PCT Filed: Aug. 25, 2021

(86) PCT No.: PCT/EP2021/073449
§ 371 (c)(1),
(2) Date: Mar. 2, 2023

(87) PCT Pub. No.: WO2022/048959
PCT Pub. Date: Mar. 10, 2022

(65) Prior Publication Data
US 2023/0263476 A1    Aug. 24, 2023

(30) Foreign Application Priority Data
Sep. 2, 2020   (EP) .................................... 20194197

(51) Int. Cl.
*A61B 5/00*    (2006.01)
*A61B 5/021*   (2006.01)
*A61B 5/022*   (2006.01)

(52) U.S. Cl.
CPC ........ *A61B 5/7221* (2013.01); *A61B 5/02116* (2013.01); *A61B 5/02225* (2013.01)

(58) Field of Classification Search
None
See application file for complete search history.

(56) References Cited

U.S. PATENT DOCUMENTS 5,178,151 A * 1/1993 Sackner ............... A61B 5/1135
                                                        600/526
6,315,735 B1 * 11/2001 Joeken .................. A61B 5/021
                                                        600/526
(Continued)

FOREIGN PATENT DOCUMENTS

EP         3669762 A1    6/2020
WO    2020126576 A1    6/2020
(Continued)

OTHER PUBLICATIONS

"Non-Invasive Cuff-less Measurements of the Arterial Blood Pressure: What does Pulse-Transit-Time tell US all about" by X. Aubert and J. Muehlsteff, Proc. European Study Group on Cardiovascular Oscillations, 211-214 (2006).
(Continued)

*Primary Examiner* — Carl H Layno
*Assistant Examiner* — Manolis Pahakis

(57) ABSTRACT

A method of estimating the reliability of cardiac output (CO) measurements obtained using an arterial waveform analysis (AWA) technique calibrated using thermodilution. During thermodilution calibration: (i) initiating inflation of a cuff that is at a location on the subject, (ii) obtaining a first cuff pressure signal comprising measurements of pressure inside the cuff during inflation, (iii) analyzing the first cuff pressure signal to derive a relationship between oscillations in arterial volume beneath the cuff and pressure in the arteries, and (iv) estimating a first arterial compliance of the arteries for a range of cuff pressures based on the determined relationship, (b) during a second time period that is after the first time period, repeating steps (i)-(iv) to estimate a second arterial compliance of the arteries, and (c) using a result of a comparison of the first arterial compliance and the second (Continued)

arterial compliance to determine a reliability of CO measurements.

15 Claims, 9 Drawing Sheets

(56) References Cited

U.S. PATENT DOCUMENTS

| | | | |
|---|---|---|---|
| 7,588,542 B2* | 9/2009 | Pfeiffer | A61B 5/029 |
| | | | 600/485 |
| 7,826,319 B2 | 11/2010 | Yamamoto | |
| 8,273,031 B2* | 9/2012 | Cohen | A61B 5/029 |
| | | | 600/485 |
| 9,668,662 B2* | 6/2017 | Whitt | A61B 5/0295 |
| 11,426,082 B2 | 8/2022 | Sakai | |
| 2002/0120204 A1* | 8/2002 | Pfeiffer | A61B 5/028 |
| | | | 600/526 |
| 2004/0158163 A1* | 8/2004 | Cohen | A61B 5/029 |
| | | | 600/513 |
| 2005/0187481 A1* | 8/2005 | Hatib | A61B 5/318 |
| | | | 600/485 |
| 2005/0267379 A1 | 12/2005 | Pfeiffer | |
| 2006/0224053 A1* | 10/2006 | Black | A61B 5/0261 |
| | | | 600/326 |
| 2006/0235323 A1* | 10/2006 | Hatib | A61B 5/0215 |
| | | | 600/526 |
| 2008/0015451 A1* | 1/2008 | Hatib | A61B 5/0295 |
| | | | 600/481 |
| 2008/0033305 A1* | 2/2008 | Hatib | A61B 5/0285 |
| | | | 600/485 |
| 2008/0287812 A1* | 11/2008 | Parlikar | A61B 5/029 |
| | | | 600/526 |
| 2009/0270739 A1* | 10/2009 | Hatib | G16H 50/50 |
| | | | 600/481 |
| 2010/0016735 A1* | 1/2010 | Harpas | A61B 5/022 |
| | | | 600/485 |
| 2010/0094144 A1* | 4/2010 | Doron | A61N 1/36564 |
| | | | 600/509 |
| 2010/0312123 A1 | 12/2010 | Phillips | |
| 2010/0317976 A1* | 12/2010 | Chelma | A61B 5/021 |
| | | | 600/485 |
| 2013/0085357 A1* | 4/2013 | Huber | A61B 5/028 |
| | | | 600/509 |
| 2013/0184595 A1* | 7/2013 | Mukkamala | A61B 5/7278 |
| | | | 600/500 |
| 2015/0018632 A1* | 1/2015 | Khair | A61N 1/36585 |
| | | | 607/18 |
| 2015/0126820 A1* | 5/2015 | Muhlsteff | A61B 5/1116 |
| | | | 600/479 |
| 2018/0214033 A1* | 8/2018 | Holland | A61B 5/02156 |
| 2018/0228386 A1* | 8/2018 | McCall | A61B 5/0215 |
| 2019/0159688 A1 | 5/2019 | De Groot | |
| 2021/0228095 A1* | 7/2021 | Pfeiffer | A61B 5/0816 |
| 2023/0000366 A1* | 1/2023 | Krogh | A61B 5/029 |

FOREIGN PATENT DOCUMENTS

| | | |
|---|---|---|
| WO | 2021001336 A1 | 1/2021 |
| WO | 2022122863 A1 | 6/2022 |

OTHER PUBLICATIONS

"Clinical review: Update on hemodynamic monitoring—a consensus of 16" by Jean-Louis Vincent Andrew Rhodes, Azriel Perel, Greg S Martin, Giorgio Della Rocca, Benoit Vallet, Michael R Pinsky, Christoph K Hofer, Jean-Louis Teboul, Willem-Pieter de Boode, Sabino Scolletta, Antoine Vieillard-Baron, Daniel De Backer, Keith R Walley, Marco Maggiorini and Mervyn Singer.
Pulse Contour Cardiac Output (PICCO) Learning Package (2016), available at: https://www.aci.health.nsw.gov.au/_data/assets/pdf_file/0005/306590/Pulse_Contour_Cardiac_Output_Learning_Package.pdf.
"A modelling framework for assessment of arterial compliance by fusion of oscillometry and pulse wave velocity information" by Bogatu, L. I., Turco, S., Mischi, M., Woerlee, P., Bouwman, A., Korsten, E. H. H. M., & Muehlsteff, J., Computer Methods and Programs in Biomedicine, 196, (2020).
International Search Report Dated Nov. 11, 2021 for International Application No. PCT/EP2021/073449 Filed Aug. 25, 2021.
Zong, W., Moody, G. and Mark, R. Effects of vasoactive drugs on the relationship between ECG-pulse wave delay time and arterial blood pressure in ICU patients"" Computers in Cardiology 1998. vol. 25 (Cat. No. 98CH36292).

\* cited by examiner

METHOD AND APPARATUS FOR ESTIMATING THE RELIABILITY OF CARDIAC OUTPUT MEASUREMENTS

CROSS-REFERENCE TO PRIOR APPLICATIONS

This application is the U.S. National Phase application under 35 U.S.C. § 371 of International Application No. PCT/EP2021/073449 filed on Aug. 25, 2021, which claims the benefit of European Application No. 20194197.8 filed on Sep. 2, 2020. These applications are hereby incorporated by reference herein.

FIELD OF THE INVENTION

This disclosure relates to a method and apparatus for estimating the reliability of cardiac output (CO) measurements for a subject, and in particular to estimating the reliability of CO measurements obtained using an arterial waveform analysis, AWA, technique.

BACKGROUND OF THE INVENTION

Cardiac output (CO) is a key hemodynamic parameter measured in critical care. CO is the volume of blood pumped by the heart per unit time. The CO is related to the heart rate (HR) and the stroke volume (SV), which is the volume of blood pumped by the heart during each beat. Due to the relevance of CO, several approaches are available for CO measurement, at various degrees of invasiveness and reliability. For example, techniques include intermittent thermodilution by pulmonary artery catheter or by the invasive access to venous and arterial sites, continuous arterial waveform analysis (AWA) of the invasively measured pressure waveform (calibrated or uncalibrated by thermodilution), esophageal Doppler, suprasternal Doppler, echocardiography, bio impedance/reactance, and partial carbon dioxide ($CO_2$) rebreathing.

Calibrated AWA can measure CO continuously and accurately and with minimal additional training for the care provider (e.g. physician, nurse, etc.). However, for accurate measurements, AWA requires repeated calibrations against another type of CO measurement, typically thermodilution.

The basic approach to infer AWA can be discussed by the simple model of the arterial network as shown in FIG. 1. FIG. 1 can also be found in "Non-Invasive Cuff-less Measurements of the Arterial Blood Pressure: What does Pulse-Transit-Time tell us all about?" by X. Aubert and J. Muehlsteff, Proc. European Study Group on Cardiovascular Oscillations, 211-214 (2006). Mathematically, the CO can be estimated from the measured pressures (which in AWA is from the invasive blood pressure waveform) and the parameter of the arterial network such as the aortic resistance (represented in FIG. 1 by the resistor having resistance $R_0$), the systemic resistance (represented in FIG. 1 by the resistor having resistance $R_s$) and the arterial network effective compliance C. Based on this model, the cardiac output (denoted $Q_a$) can be given by:

$$Q_a(t) = \frac{p_a(t) - p_s(t)}{R_0} = \frac{1}{R_0 + R_s}\left[p_a(t) + R_s \cdot C_s(p_s)\frac{dp_s}{dt}\right] \quad (1)$$

where $p_a$ is the arterial pressure and $p_s$ is the systemic pressure.

Currently these parameters cannot be, or are not, easily measured in clinical practice. As a practical approach, C, $R_0$ and R are therefore treated as open parameters, which are "calibrated" via intermittent thermodilution which provides a reference CO measurement, and the parameters are then held constant. In a thermodilution measurement, a heated or cooled fluid is introduced into the blood flow, and temperature (bolus temperature) is measured at different sites in the circulatory system. In a transpulmonary thermodilution measurement, temperature changes can be measured between a central venous line and a central arterial line.

SUMMARY OF THE INVENTION

Thus, once determined via calibration (e.g. a thermodilution measurement), the parameters C, $R_0$ and R are than held constant. However, there is a risk of an unrecognised physiological change in the subject that would make a CO inference based on these parameters invalid, and thus current haemodynamic monitoring practices have the limitation that it is difficult to obtain a reliable estimation of cardiac output between intermittent thermodilution measurements. In particular, a change in arterial compliance (C) from when the thermodilution calibration measurement was made can lead to an incorrect interpretation of the arterial pressure waveform and therefore an incorrect estimation of cardiac output, as described in "Clinical review: Update on hemodynamic monitoring—a consensus of 16" by Jean-Louis Vincent Andrew Rhodes, Azriel Perel, Greg S Martin, Giorgio Della Rocca, Benoit Vallet, Michael R Pinsky, Christoph K Hofer, Jean-Louis Teboul, Willem-Pieter de Boode, Sabino Scolletta, Antoine Vieillard-Baron, Daniel De Backer, Keith R Walley, Marco Maggiorini and Mervyn Singer. There is no clinically implemented direct modality for identifying alterations in arterial compliance, and as a result there is uncertainty in the reliability of waveform-based CO measurements.

In typical clinical practice, intermittent thermodilution calibrations have been recommended every few hours. This is problematic since a time-based re-calibration ignores physiological changes that can occur between calibrations, and the human body continuously regulates CO on much smaller time scales. As a result, the accuracy of CO obtained by AWA is typically limited and results in incorrect diagnostics, decisions and treatments, and ultimately in compromised patient outcomes.

Therefore, it is desirable to provide techniques for estimating the reliability of CO measurements obtained using an AWA technique.

According to a first specific aspect, there is provided a method of estimating the reliability of cardiac output, CO, measurements for a subject obtained using an arterial waveform analysis, AWA, technique. The AWA technique is calibrated using CO measurements obtained using a thermodilution CO measurement technique. The method comprises (a) during a first time period in which a first CO measurement is obtained for the subject using the thermodilution CO measurement technique: (i) initiating inflation of a cuff that is at a first location on the subject; (ii) obtaining a first cuff pressure signal comprising measurements of pressure inside the cuff during inflation; (iii) analysing the first cuff pressure signal to derive a relationship between oscillations in arterial volume beneath the cuff and pressure in the arteries; and (iv) estimating a first arterial compliance of the arteries for a range of cuff pressures based on the determined relationship; (b) during a second time period that is after the first time period, repeating steps (i)-(iv) to estimate a second arterial compliance of the arteries; and (c) using a result of a comparison of the first arterial compliance and the second arterial compliance to determine a reliability of CO measurements obtained using the AWA technique during the second time period.

In some embodiments, if the CO measurements obtained using the AWA technique during the second time period are determined to be reliable, then method can further comprise (d) during a third time period that is after the second time period repeating steps (i)-(iv) to estimate a third arterial compliance of the arteries; and (e) repeating step (c) using the second arterial compliance and the third arterial compliance. In this way the reliability of the CO measurements can be continuously or periodically assessed.

In some embodiments, if the CO measurements obtained using the AWA technique during the second time period are determined to be unreliable, the method can further comprise one or more of: initiating the thermodilution CO measurement technique to obtain a second CO measurement and calibrating the AWA technique using the second CO measurement; indicating the unreliability of the measurements obtained using the AWA technique to a user; and determining an adjustment to a value of an arterial compliance parameter used in the AWA technique based on the result of the comparison. In the first case, when the CO measurements are determined to be unreliable a recalibration can be automatically triggered. In the second case, when the CO measurements are determined to be unreliable a user can be informed and can manually trigger a recalibration. In the third case, a recalibration procedure can be avoided by making an adjustment to the arterial compliance parameter used in the AWA technique.

In some embodiments, the method further comprises determining one or more CO measurements using the AWA technique.

In some embodiments, the method further comprises obtaining a photoplethysmogram, PPG, signal and/or an electrocardiogram, ECG, signal for the subject when steps (i) and (ii) are performed; and analysing the PPG signal and/or the ECG signal to determine a first pulse arrival time, PAT, and/or a first pulse wave velocity, PWV, for the subject. Step (iv) comprises estimating the first arterial compliance of the arteries for the range of cuff pressures based on the determined relationship and the first PAT and/or the first PWV. This embodiment provides an improved estimate of the first arterial compliance. In these embodiments, the method can further comprise: after step (iv), obtaining a further PPG signal and/or a further ECG signal for the subject; analysing the further PPG signal and/or the further ECG signal to determine a second PAT for the subject; comparing the second PAT to the first PAT; and determining whether to perform step (b) based on the result of the comparison of the second PAT to the first PAT. These embodiments provide a simple way to monitor the subject to determine when the arterial compliance may have changed, and which can be used to trigger a more accurate measurement of arterial compliance using the cuff. In these embodiments, the step of determining whether to perform step (b) can comprise determining that step (b) is to be performed if a difference between the second PAT and the first PAT is greater than a threshold, and otherwise determining not to perform step (b).

In alternative embodiments, the second time period is a predefined time after the first time period. In this way, an arterial compliance checked using the cuff is performed on a regular basis so that changes to arterial compliance can be detected.

In alternative embodiments, the method further comprises obtaining a PPG signal for the subject when steps (i) and (ii) are performed; analysing the PPG signal to determine a first PPG morphology; after step (iv), obtaining a further PPG signal for the subject; analysing the further PPG signal to determine a second PPG morphology; comparing the second PPG morphology to the first PPG morphology; and determining whether to perform step (b) based on the result of the comparison of the second PPG morphology to the first PPG morphology. These embodiments provide another simple way to monitor the subject to determine when the arterial compliance may have changed, and which can be used to trigger a more accurate measurement of arterial compliance using the cuff.

In some embodiments, the method further comprises obtaining an arterial pressure, AP, signal for the subject representing the AP of the subject when steps (i) and (ii) are performed; and step (iii) comprises analysing the first cuff pressure signal and the AP signal to derive the relationship between oscillations in arterial volume beneath the cuff and pressure in the arteries. The use of AP measurements improves the accuracy of the estimated relationship. In these embodiments, the cuff can be on a first arm of the subject, and the AP signal is obtained from the same arm of the subject.

According to a second aspect, there is provided a computer program product comprising a computer readable medium having computer readable code embodied therein, the computer readable code being configured such that, on execution by a suitable computer or processor, the computer or processor is caused to perform the method according to the first aspect or any embodiment thereof.

In some embodiments, the suitable computer or processor is configured to any of: connect to a pump associated with the cuff; connect to a non-invasive blood pressure measurement device that comprises the cuff; and connect to a cuff pressure sensor that outputs the first cuff pressure signal. In further embodiments, the suitable computer or processer can be configured to any of: connect to a PPG sensor; and connect to an ECG sensor.

According to a third specific aspect, there is provided an apparatus for estimating the reliability of CO measurements for a subject obtained using an AWA technique. The AWA technique is calibrated using CO measurements obtained using a thermodilution CO measurement technique. The apparatus comprises a processing unit is configured to (a) during a first time period in which a first CO measurement is obtained for the subject using the thermodilution CO measurement technique: (i) initiate inflation of a cuff that is at a first location on the subject; (ii) obtain a first cuff pressure signal comprising measurements of pressure inside the cuff during inflation; (iii) analyse the first cuff pressure signal to derive a relationship between oscillations in arterial volume beneath the cuff and pressure in the arteries; and (iv) estimate a first arterial compliance of the arteries for a range of cuff pressures based on the determined relationship; (b) during a second time period that is after the first time period, repeat functions (i)-(iv) to estimate a second arterial compliance of the arteries; and (c) use a result of a comparison of the first arterial compliance and the second arterial compliance to determine a reliability of CO measurements obtained using the AWA technique during the second time period.

In some embodiments, the processing unit is further configured to, if the CO measurements obtained using the AWA technique during the second time period are determined to be reliable, (d) during a third time period that is after the second time period repeat functions (i)-(iv) to estimate a third arterial compliance of the arteries; and (e) repeat function (c) using the second arterial compliance and the third arterial compliance. In this way the reliability of the CO measurements can be continuously or periodically assessed.

In some embodiments, the processing unit is further configured to, if the CO measurements obtained using the AWA technique during the second time period are determined to be unreliable, one or more of: initiate the thermodilution CO measurement technique to obtain a second CO measurement and calibrate the AWA technique using the second CO measurement; indicate the unreliability of the measurements obtained using the AWA technique to a user; and determine an adjustment to a value of an arterial compliance parameter used in the AWA technique based on the result of the comparison. In the first case, when the CO measurements are determined to be unreliable a recalibration can be automatically triggered. In the second case, when the CO measurements are determined to be unreliable a user can be informed and can manually trigger a recalibration. In the third case, a recalibration procedure can be avoided by making an adjustment to the arterial compliance parameter used in the AWA technique.

In some embodiments, the processing unit is further configured to determine one or more CO measurements using the AWA technique.

In some embodiments, the processing unit is further configured to obtain a PPG signal and/or an ECG signal for the subject when functions (i) and (ii) are performed; and analyse the PPG signal and/or the ECG signal to determine a first PAT and/or a first PWV for the subject. Function (iv) comprises estimating the first arterial compliance of the arteries for the range of cuff pressures based on the determined relationship and the first PAT and/or the first PWV. This embodiment provides an improved estimate of the first arterial compliance. In these embodiments, the processing unit is further configured to, after function (iv), obtain a further PPG signal and/or a further ECG signal for the subject; analyse the further PPG signal and/or the further ECG signal to determine a second PAT for the subject; compare the second PAT to the first PAT; and determine whether to perform function (b) based on the result of the comparison of the second PAT to the first PAT. These embodiments provide a simple way to monitor the subject to determine when the arterial compliance may have changed, and which can be used to trigger a more accurate measurement of arterial compliance using the cuff. In these embodiments, the processing unit can be configured to determine that function (b) is to be performed if a difference between the second PAT and the first PAT is greater than a threshold, and otherwise determining not to perform function (b).

In alternative embodiments, the second time period is a predefined time after the first time period. In this way, an arterial compliance checked using the cuff is performed on a regular basis so that changes to arterial compliance can be detected.

In alternative embodiments, the processing unit is further configured to obtain a PPG signal for the subject when functions (i) and (ii) are performed; analyse the PPG signal to determine a first PPG morphology; after function (iv), obtain a further PPG signal for the subject; analyse the further PPG signal to determine a second PPG morphology; compare the second PPG morphology to the first PPG morphology; and determine whether to perform function (b) based on the result of the comparison of the second PPG morphology to the first PPG morphology. These embodiments provide another simple way to monitor the subject to determine when the arterial compliance may have changed, and which can be used to trigger a more accurate measurement of arterial compliance using the cuff.

In some embodiments, the processing unit is further configured to obtain an AP signal for the subject representing the AP of the subject when functions (i) and (ii) are performed; and function (iii) comprises analysing the first cuff pressure signal and the AP signal to derive the relationship between oscillations in arterial volume beneath the cuff and pressure in the arteries. The use of AP measurements improves the accuracy of the estimated relationship. In these embodiments, the cuff can be on a first arm of the subject, and the AP signal is obtained from the same arm of the subject.

In some embodiments, the apparatus further comprises, or comprises one or more interfaces to enable connection to, one or more of: the cuff, a pump for the cuff, and a cuff pressure sensor that measures the pressure in the cuff and that outputs the first cuff pressure signal.

According to a fourth specific aspect, there is provided a system for estimating the reliability of CO measurements for a subject obtained using an AWA technique. The system comprises an apparatus according to the third aspect or any embodiment thereof, and one or more of the cuff, a pump for the cuff, and a cuff pressure sensor that measures the pressure in the cuff and that outputs the first cuff pressure signal.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
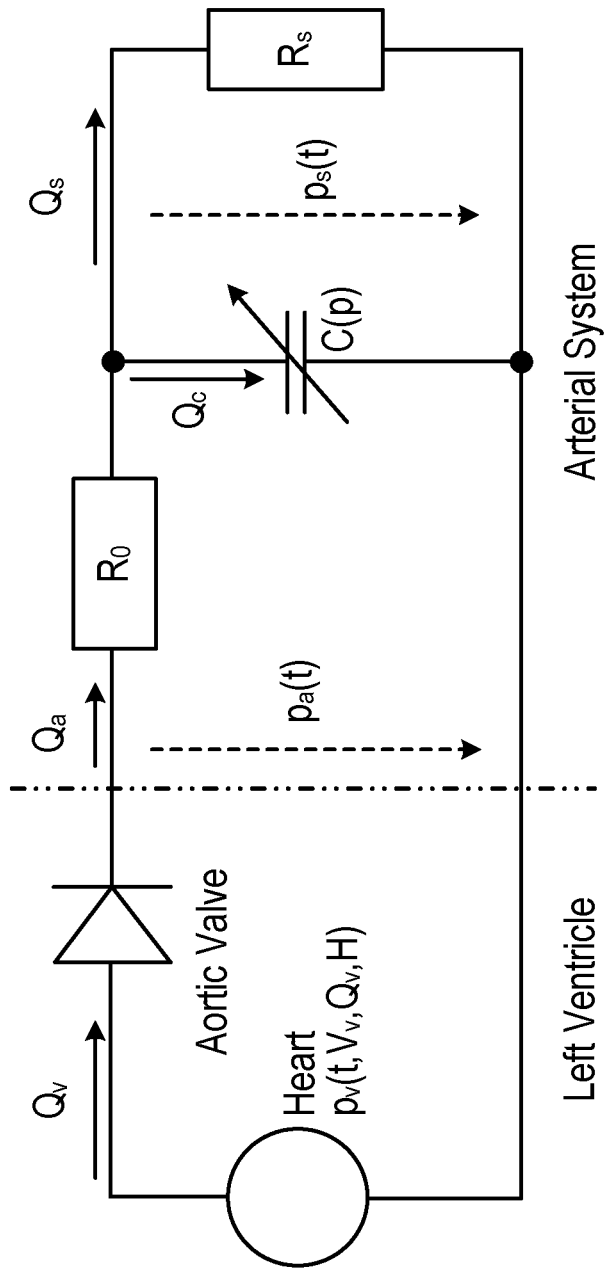
FIG. 1 is a model of the arterial network.

As noted, techniques are provided for estimating the reliability of cardiac output (CO) measurements obtained using an AWA technique. In particular, the techniques aim to identify when a change in arterial compliance (C) of the subject has occurred since a calibration measurement was made, since changes in arterial compliance are recognised as a main cause of CO calibration drift (e.g. as described in "Clinical review: Update on hemodynamic monitoring—a consensus of 16"). These changes can lead to an incorrect interpretation of the arterial pressure waveform and therefore an incorrect estimation of cardiac output. The change in arterial compliance provides an indication of the reliability of CO measurements obtained using the AWA technique. For example, if the arterial compliance has not changed, or has not changed by more than a threshold amount, then the CO measurements obtained using AWA can be deemed reliable, or sufficiently reliable, and/or if the arterial compliance has changed, or has changed by more than a threshold amount, then the CO measurements obtained using AWA can be deemed unreliable. This indication of reliability of the AWA-obtained CO measurements can be used to determine if a new calibration measurement should be made using the thermodilution technique. Alternatively (or in addition), and particularly in the case of small changes in the arterial compliance, the indication of reliability of the AWA-obtained CO measurements can be used to determine adjustments to the value of C (the arterial compliance) used in the AWA model.

In the present disclosure, the term "calibration procedure" refers to a procedure in which a measurement of cardiac output of a subject is obtained by a measurement technique other than AWA (such as thermodilution) and used to calibrate (i.e. determine values for) the parameters used in the model for AWA-based measurements of CO. The CO measurement obtained using the calibration procedure is referred to herein as the "calibration CO measurement". The measurement technique used for the calibration procedure is preferably thermodilution, although other techniques such as measuring CO via dye solutions, echo or carbon dioxide (CO2) rebreathing, can be used. The term "thermodilution CO measurement" refers to a CO measurement obtained using thermodilution. The term "AWA CO measurement" is used herein to refer to a measurement of cardiac output obtained using the AWA technique, where the AWA model has been calibrated using the calibration procedure. Those skilled in the art will be aware of the details of the AWA technique, with, for example, further details being found in the Pulse Contour Cardiac Output (PICCO) Learning Package (2016), available at: https://www.aci.health.nsw.gov.au/_data/assets/pdf_file/0005/306590/Pulse_Contour_Cardiac_Output_Learning_Package.pdf.

Various embodiments are proposed herein to enable the reliability of CO measurements obtained using the AWA technique to be estimated. In particular, a cuff-based non-invasive blood pressure (NIBP) measurement device (or at least a cuff and a sensor for measuring pressure oscillations in the cuff) is used to obtain information on the arterial compliance when (i.e. at the same time as) the calibration procedure is performed. The use of a cuff enables an estimation of arterial compliance to be obtained from information on arterial volume versus the applied cuff pressure (which results in an effective transmural pressure being applied to the arteries). According to various embodiments, a change in arterial compliance can then be identified by evaluating further pressure oscillation signals and/or measurement signals from one or more other types of sensors, such as a photoplethysmography, PPG, sensor (or other type of pulse oximetry sensor), an electrocardiogram, ECG, sensor, and/or an (invasive) arterial pressure, AP, sensor. These types of sensors are typically applied to, or are at least available to be applied to, subjects that are undergoing CO measurement by thermodilution, since thermodilution measurements are typically performed in a clinical environment. In embodiments where a PPG sensor and/or an ECG sensor are present, these sensors can be used to derive or determine pulse arrival time (PAT), which is related to pulse wave velocity (PWV), and which is itself related to arterial compliance.

NIBP measurement devices can be set to automatically obtain cuff-based blood pressure (BP) measurements, for example, every 5 to 60 minutes, and a PPG sensor or an ECG sensor can provide beat-to-beat waveforms. As a result, it can be possible to detect changes in arterial compliance over relatively short timescales, e.g. of the order of minutes.

If a significant arterial compliance change is detected, indicating that an AWA CO measurement may be unreliable, then one or more actions can be taken. One action is to flag to a care provider (e.g. via a display or other user interface component on a patient monitor that arterial compliance may have changed, which could, for example, prompt the care provider to perform or trigger the calibration procedure. Another action is to automatically trigger the calibration procedure. Another action is to correct or adjust the arterial compliance parameter value in the AWA model according to the detected change in arterial compliance.

Figure 2:
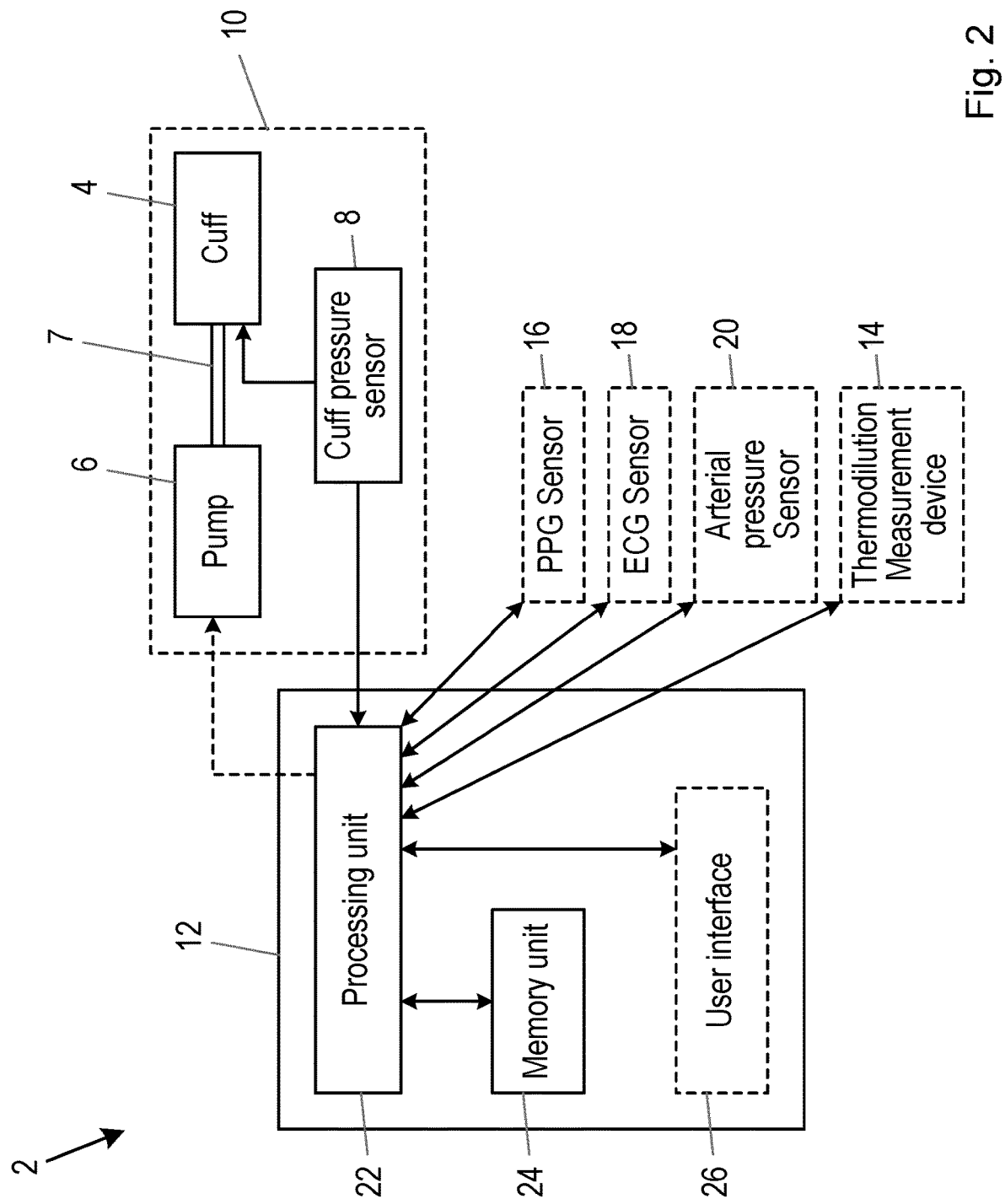
FIG. 2 is a block diagram of an apparatus that can be used to implement the techniques described herein.

FIG. 2 is a block diagram of a system 2 according to various embodiments for estimating the reliability of cardiac output measurements for a subject obtained using AWA.

The system 2 comprises a cuff 4, a pump 6 that is connected to the cuff 4 (e.g. via a connecting tube 7) and a cuff pressure sensor 8 for measuring the pressure in the cuff 4. The cuff 4 is to be placed around a body part of a subject of interest, e.g. around a limb such as an arm or leg, and the pump 6 is controllable to selectively inflate the cuff 4. The pump 6 may also be able to selectively deflate the cuff 4, and/or a valve (not shown) may be provided for enabling the cuff 4 to be deflated. The cuff pressure sensor 8 measures the pressure in the cuff 4, at least when the cuff 4 is applying a defined stimulus on the artery located under the cuff 4 (this can be during inflation of the cuff 4, deflation of the cuff 4, or while the pressure in the cuff 4 is held at a particular level). The cuff pressure sensor 8 outputs a cuff pressure signal that represents, or relates to, the pressure in the cuff 4 over time. The cuff 4, pump 6 and cuff pressure sensor 8 may be part of a NIBP measurement device 10, and may comprise one or more further components that are configured to process the signal from the cuff pressure sensor 8 to determine the blood pressure of the subject. Alternatively, the system 2 may not comprise a NIBP measurement device 10, and the cuff 4, pump 6 and cuff pressure sensor 8 may be provided specifically for use by the system 2 in determining the reliability of CO measurements obtained using AWA.

The system 2 also comprises an apparatus 12 that operates according to the techniques described herein to determine the reliability of CO measurements obtained using AWA. The apparatus 12 is configured to receive the cuff pressure measurement signal from the cuff pressure sensor 8. In some embodiments, the apparatus 12 is configured to control the operation of the pump 6, and thereby initiate the inflation of the cuff 4 at an appropriate time.

In some embodiments, in addition to estimating the reliability of the AWA CO measurements, the apparatus 12 can also be configured to determine the AWA CO measurements. Thus, in some embodiments, the apparatus 12 is configured to implement conventional AWA-based CO measurement techniques to determine AWA CO measurements.

The apparatus 12 may be in the form of, or be part of, a computing device, such as a server, desktop computer, laptop, tablet computer, smartphone, smartwatch, etc., or other types of device typically found in clinical environments, such as a patient monitoring device (e.g. a monitoring device located at the bedside of a patient in a clinical environment) that is used to monitor (and optionally display) various physiological characteristics of a subject/patient.

In embodiments where the cuff 4, pump 6 and cuff pressure sensor 8 are provided specifically for use by the system 2 in determining the reliability of AWA CO measurements, the apparatus 12 may also be configured to process the signal from the cuff pressure sensor 8 to determine the blood pressure of the subject.

The system 2 may also comprise a thermodilution measurement device 14 that is used to obtain a measurement of cardiac output of the subject, and that is obtained and used during the calibration procedure. The thermodilution measurement device 14 may be or comprise one or more temperature sensors that can be positioned at respective sites of the arterial and/or venous system of the subject, and that measure the bolus temperature of the blood at those sites over time. The thermodilution measurement device 14 may also include a mechanism to enable a heated or cooled fluid to be controllably introduced into the blood of the subject. The thermodilution measurement device 14 may comprise one or more further components that are configured to process signal(s) from the temperature sensor(s) to determine the CO measurement (i.e. the calibration CO measurement). Alternatively, the signal(s) from the temperature sensor(s) may be provided to the apparatus 12, and the apparatus 12 can determine the CO measurement by analysing the temperature signal(s).

In some embodiments, the system 2 can comprise one or more additional sensors that are used to measure physiological characteristics of the subject/patient.

The additional sensor(s) can comprise one or more PPG sensors 16 that are to be placed on the body of the subject and that output a PPG signal that is related to the volume of blood passing through that part of the body. As known to those skilled in the art, a PPG sensor 16 comprises a light sensor, and typically one or more light sources. The PPG signal output by the PPG sensor(s) 16 may be a raw measurement signal from the light sensor (e.g. the PPG signal can be a signal representing light intensity over time), or the PPG sensor(s) 16 may perform some processing of the light intensity signal to determine values of one or more physiological characteristics, such as heart rate, oxygen saturation, etc. In that case, the PPG signal is a time-series of measurements of that/those physiological characteristics.

The additional sensor(s) can comprise an ECG sensor 18 that is to be placed on the body of the subject and that outputs an ECG signal that is related to the electrical activity of the heart of the subject. As known to those skilled in the art, an ECG sensor 18 comprises a plurality of electrodes that are placed on different parts of the body, and the ECG signal can include one or more signals representing the voltage measured by the electrodes over time. The ECG signal output by the ECG sensor 18 may be a raw measurement signal(s) from the electrodes, or the ECG sensor 18 may perform some processing of the voltage measurements to determine values of one or more physiological characteristics, such as heart rate, heart rate variability, etc. In that case, the ECG signal is a time-series of measurements of that/those physiological characteristics.

Where the system 2 or apparatus 12 itself is to determine the AWA CO measurements, the additional sensor(s) can comprise an arterial pressure (AP) sensor 20. The AP sensor 20 is a sensor that is used invasively (i.e. used inside an artery, or that otherwise requires access to an artery) and so the AP sensor 20 is to be placed at a measurement site in the arterial system of the body of the subject. The AP sensor 20 measures the arterial pressure and outputs an AP signal that is related to the pressure of the blood in the arteries at the measurement site. The AP signal output by the AP sensor 20 may be a raw measurement signal representing the arterial pressure waveform over time. In embodiments where the system 2 or apparatus 12 determines the AWA CO measurement, the system 2 or apparatus 12 analyses the AP signal to determine the CO according to the AWA technique.

The apparatus 12 includes a processing unit 22 that controls the operation of the apparatus 12 and that can be configured to execute or perform the methods described herein. The processing unit 22 can be implemented in numerous ways, with software and/or hardware, to perform the various functions described herein. The processing unit 22 may comprise one or more microprocessors or digital signal processors (DSPs) that may be programmed using software or computer program code to perform the required functions and/or to control components of the processing unit 22 to effect the required functions. The processing unit 22 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 22 is connected to a memory unit 24 that can store data, information and/or signals for use by the processing unit 22 in controlling the operation of the apparatus 12 and/or in executing or performing the methods described herein. In some implementations the memory unit 24 stores computer-readable code that can be executed by the processing unit 22 so that the processing unit 22 performs one or more functions, including the methods described herein. In particular embodiments, the program code can be in the form of an application for a smartwatch, smartphone, tablet, laptop or computer. The memory unit 24 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit 24 can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments, the apparatus 12 comprises a user interface 26 that includes one or more components that enables a user of apparatus 12 to input information, data and/or commands into the apparatus 12, and/or enables the apparatus 12 to output information or data to the user of the apparatus 12. Information that can be output by the user interface 26 can include any of: an indication of the reliability of an AWA CO measurement, an AWA CO measurement, an indication of the arterial compliance, or an indication of a change in arterial compliance since a calibration procedure was last performed, an indication that a calibration procedure should be performed to obtain a new calibration CO measurement, and the calibration CO measurement. The user interface 26 can comprise any suitable input component(s), including but not limited to a keyboard, keypad, one or more buttons, switches or dials, a mouse, a track pad, a touchscreen, a stylus, a camera, a microphone, etc., and/or the user interface 26 can comprise any suitable output component(s), including but not limited to a display screen, one or more lights or light elements, one or more loudspeakers, a vibrating element, etc.

It will be appreciated that a practical implementation of an apparatus 12 may include additional components to those shown in FIG. 2. For example the apparatus 12 may also include a power supply, such as a battery, or components for enabling the apparatus 12 to be connected to a mains power supply. The apparatus 12 may also include interface circuitry for enabling a data connection to and/or data exchange with other devices, including any one or more of the NIBP measurement device 10 (or a separate cuff pressure sensor 8), sensors 16, 18, 20, servers, databases and user devices.

Figure 3:
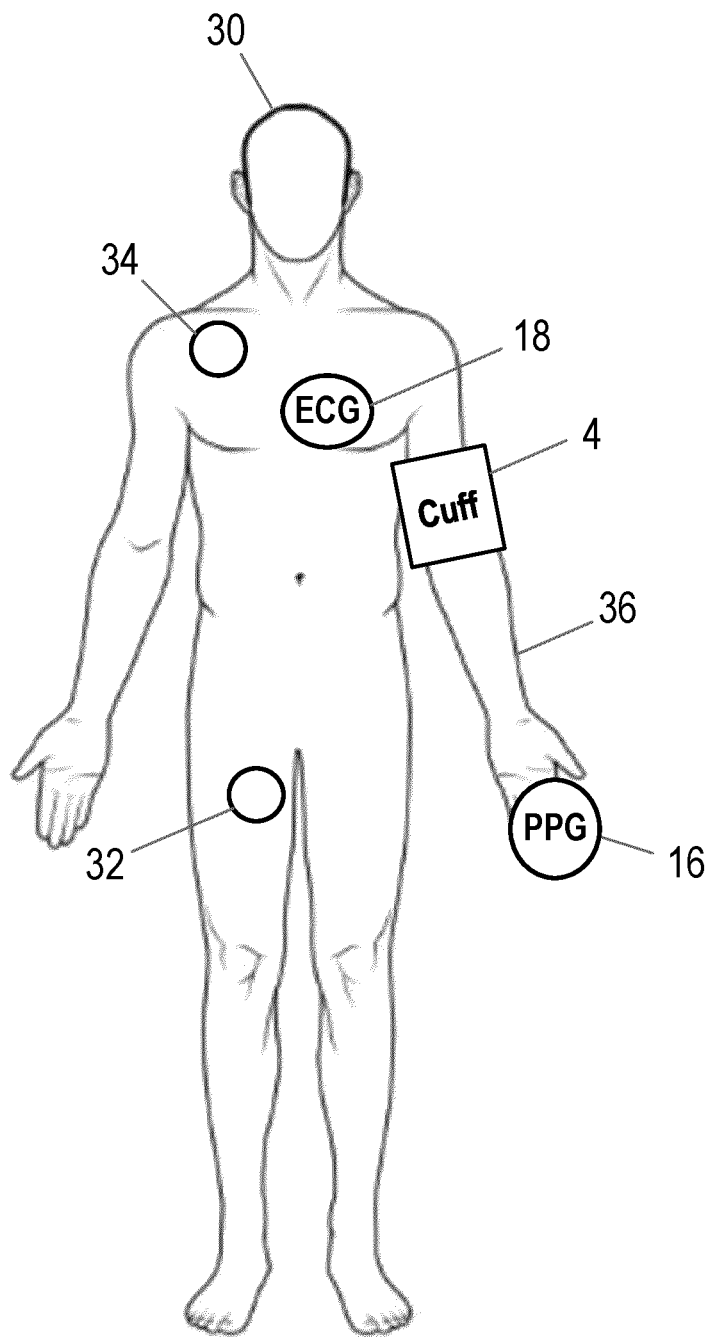
FIG. 3 is an illustration of an exemplary measurement setup on a subject according to an embodiment in which there is arterial invasive access on a different part of the body on which a cuff is placed.

FIG. 3 illustrates an exemplary measurement setup on a subject according to a first exemplary set of embodiments. In this set of embodiments, the reliability of AWA CO measurements is estimated without making use of arterial pressure measurements obtained invasively (e.g. without making use of AP signal from AP sensor 20). In these embodiments the arterial access site for the thermodilution measurement and the AP sensor 20 is typically not on the same limb (e.g. arm) as the cuff 4. However, it will be appreciated that in some implementations of the first set of embodiments, the arterial access site for the thermodilution measurement can be on the same limb as the cuff 4, but the arterial pressure measurements are not used in the method to estimate the reliability of the AWA CO measurements.

FIG. 3 shows a subject 30 for whom a thermodilution CO measurement is performed via invasive access to an arterial site 32 and a venous site 34. The arterial access can be at any of femoral, axillary, brachial or radial artery sites, and in FIG. 3 the arterial access site is shown to be at a femoral artery access site 32. The venous access can also be any of femoral, axillary, brachial or radial vein sites. In FIG. 3 the venous access site is shown to be at an axillary vein access site 34. Temperature sensors (e.g. thermistors) will typically be present in each of the sites to enable the thermodilution measurement to be made. More specifically, in a thermodilution measurement, an ice-cold saline solution is injected into the body via a central venous line, and a change in temperature can be measured distally via an arterial line catheter equipped with a thermistor or other temperature sensor. Although not shown in FIG. 3, the AP sensor 20 is typically located at the same arterial access site used for thermodilution (e.g. the femoral site 32 in FIG. 3), but it could be located in a different part of the arterial system. The AP sensor 20 measures arterial pressure and outputs an AP signal, which is also referred to as the arterial blood pressure (ABP) waveform.

The cuff 4 is placed on the left arm 36 of the subject 30, and FIG. 3 also shows PGG sensor 16 placed on the left hand (or on one or more fingers of the left hand) of the subject 30, and ECG sensor 18 is placed in the region of the heart of the subject 30 (in the typical way for ECG sensors). The PPG sensor 16 should be present on the same limb as the cuff 4. As noted below, in some embodiments the PPG sensor 16 and/or the ECG sensor 18 are not required.

Figure 4:
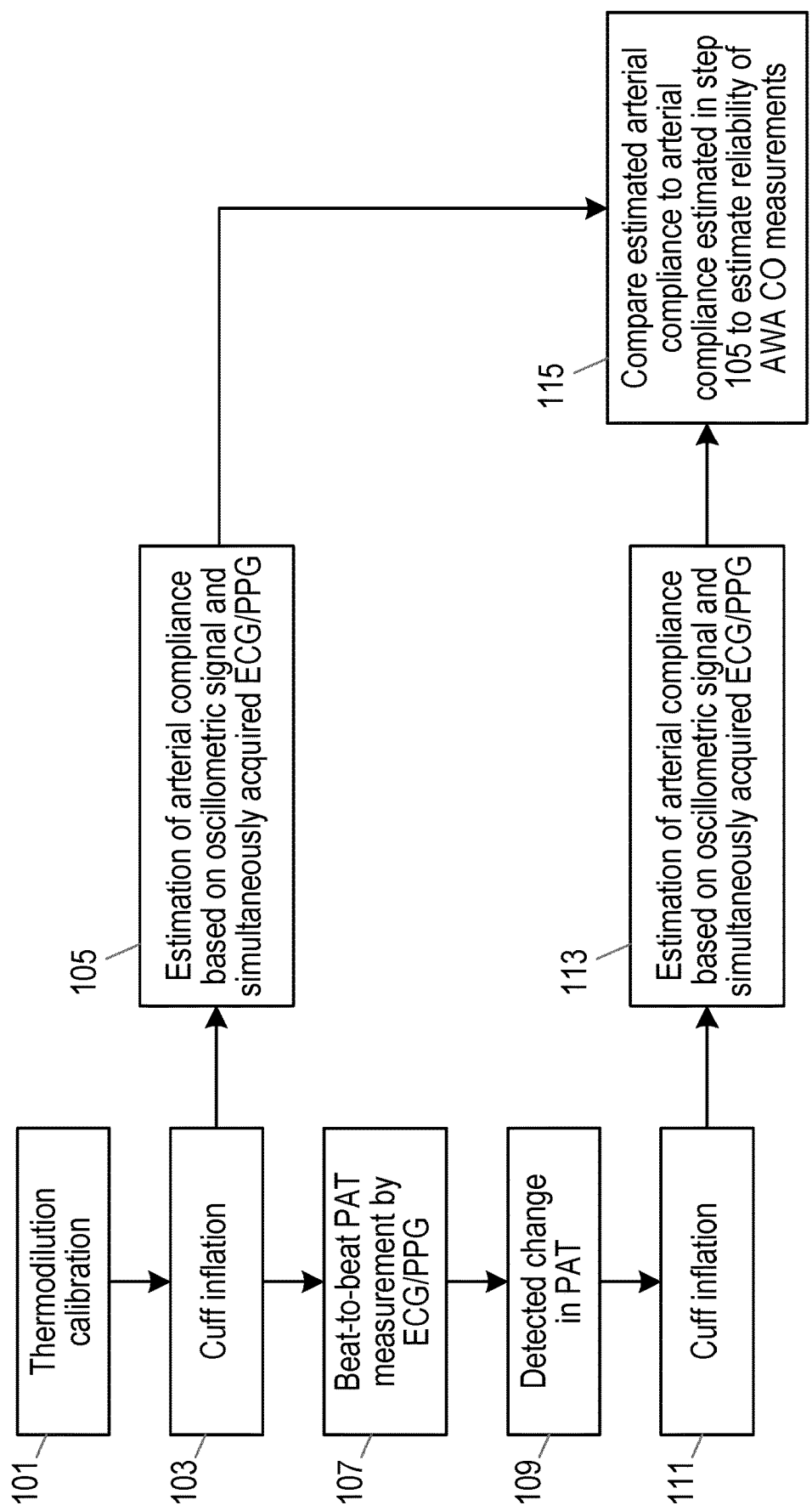
FIG. 4 is a flow chart illustrating a method of determining the reliability of AWA CO measurements according to a first specific embodiment.

In a first specific embodiment, the reliability of AWA CO measurements for a subject 30 is estimated using measurements of pressure oscillations in the cuff 4 and one or both of a PPG signal from PPG sensor 16 and an ECG signal from ECG sensor 18. An exemplary method according to this embodiment is shown in FIG. 4. One or more of the steps in FIG. 4 can be performed by the system 2, apparatus 12 and/or processing unit 22.

In step 101 a calibration procedure is performed to determine a calibration CO measurement that is used to calibrate the AWA technique for the subject 30. In particular, a thermodilution-based calibration procedure is performed to obtain one or more measurements of cardiac output of the subject 30. The calibration CO measurement is used to determine values for the parameters used in the AWA model, and in particular a value for the arterial compliance, C. This calibration step is performed in a conventional way.

At the time that the thermodilution CO measurement procedure is performed (e.g. at the same time, or during the thermodilution CO measurement procedure), the cuff 4 is inflated so that it applies pressure to the limb (e.g. arm 36). This is shown as step 103. During the inflation (and optionally also during subsequent deflation) of the cuff 4, the cuff pressure sensor 8 measures the pressure oscillations in the cuff 4 and outputs a cuff pressure signal. The PPG sensor 16 and/or ECG sensor 18 also operate during inflation of the cuff 4 and output respective signals relating to the period of cuff inflation.

The cuff pressure signal is analysed to obtain information on arterial size/volume over a range of arterial wall transmural pressures, with the transmural pressure being varied by the inflation and/or deflation of the cuff 4. The cuff pressure signal is also processed to determine a measurement of blood pressure of the subject 30. This results in a relationship between oscillations in arterial volume beneath the cuff 4 and pressure in the arteries being derived.

The PPG signal and/or ECG signal (as appropriate) obtained during step 103 are analysed to estimate a pulse arrival time (PAT) for the subject 30. The estimated PAT provides an indication of the pulse wave velocity (PWV) over a range of arterial wall transmural pressures (as applied by the cuff 4) along the artery in the limb on which the PPG sensor 16 is attached. A pulse transit time (PTT) can be determined in addition to or instead of the PAT by using the PPG signal and the ECG signal, the ECG signal and the AP signal, or the PPG signal and the AP signal.

Figure 5:
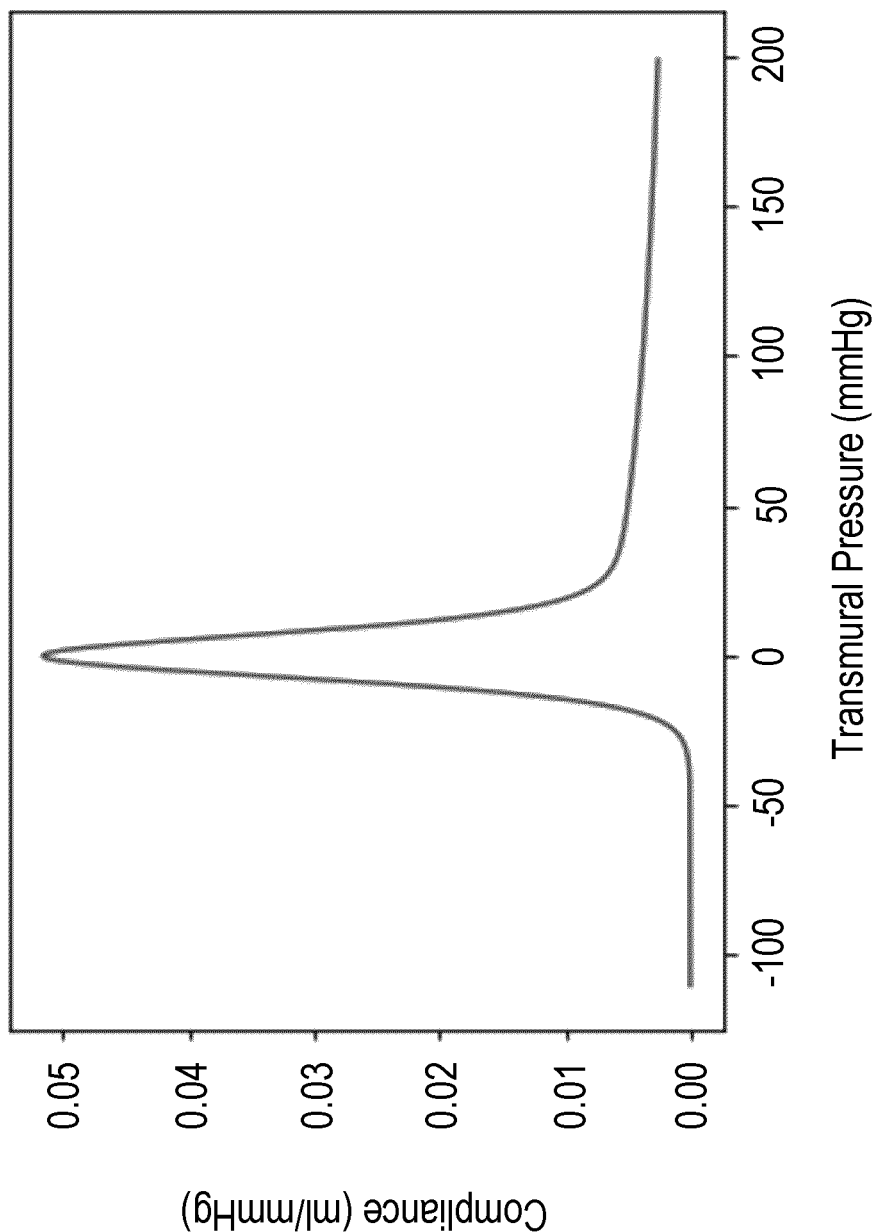
FIG. 5 is a graph illustrating arterial compliance values over a range of transmural pressures at the time that a calibration procedure was performed.

In step 105, the derived relationship between oscillations in arterial volume and arterial pressure and the estimated pulse wave velocity can be analysed to obtain an estimate of arterial compliance for the subject 30 over a range of transmural pressures. This estimate of arterial compliance is considered as a 'baseline arterial compliance', as it is an estimate of the arterial compliance at the time that the calibration procedure was performed. The graph in FIG. 5 illustrates arterial compliance values over a range of transmural pressures at the time that a calibration procedure was performed.

Those skilled in the art will be aware of various different methods that can be used to estimate arterial compliance non-invasively from oscillometry (i.e. measurements of oscillations in arterial pressure) and/or PAT-derived PWV, and further details are not provided herein. However, some exemplary techniques that can be used are described in WO 2020/126576, and International (PCT) Patent Application no. PCT/EP2020/068331.

Following the thermodilution calibration procedure, the AP sensor 20 is used to measure the arterial pressure over time, and the AP signal is evaluated using the calibrated AWA model to determine CO measurements. As noted previously, during this time it is possible that the arterial compliance can change, and this can result in the AWA CO measurement becoming unreliable.

Therefore, in this embodiment, to identify when the arterial compliance may have changed, after the baseline arterial compliance is estimated in step 105, the PPG sensor 16 and/or ECG sensor 18 continue to measure their respective parameters over time and output measurement signals (step 107). These measurement signals are analysed to determine the PAT of the subject 30. In some embodiments, the PAT of the subject 30 can be determined on a beat-to-beat basis. A change in PAT can (but not necessarily) be due to a change in arterial compliance.

Therefore, in step 109 the PAT of the subject 30 determined in step 107 is compared to the PAT determined in step 103/105. If the PAT has not changed, or the difference between the PAT estimates is within an acceptable margin (e.g. the magnitude of the difference is less than a threshold amount, or the percentage change is less than a threshold amount), then it is considered that the arterial compliance has not changed by an amount that would render the AWA CO measurements unreliable, and the method returns to step 107 and repeats.

However, if the PAT has changed, or the difference between the PAT estimates is greater than an acceptable margin (e.g. the magnitude of the difference is greater than a threshold amount, or the percentage change is more than a threshold amount), then it is possible that the arterial compliance has changed by an amount that would render the AWA CO measurements unreliable. However, although changes in arterial compliance lead to changes in PAT, not all changes in PAT are due to changes in arterial compliance, and so beat-to-beat PAT is not sufficient to indicate a change in arterial compliance. This is because PAT alterations can occur due to changes in arterial smooth muscle tone, but also due to changes in blood pressure or heart pre-ejection periods. Therefore, when a change or sufficient change in PAT is detected in step 109, it is necessary to determine another estimate of arterial compliance using an oscillometric signal from the cuff pressure sensor 8. Therefore, when a change or sufficient change in PAT is detected in step 109, a cuff inflation procedure similar to that in steps 103 and 105 is performed so that a further estimate of arterial compliance is obtained (step 111 and 113). As in step 105, step 113 provides a further estimate of arterial compliance for the subject 30 over a range of transmural pressures.

Figure 6:
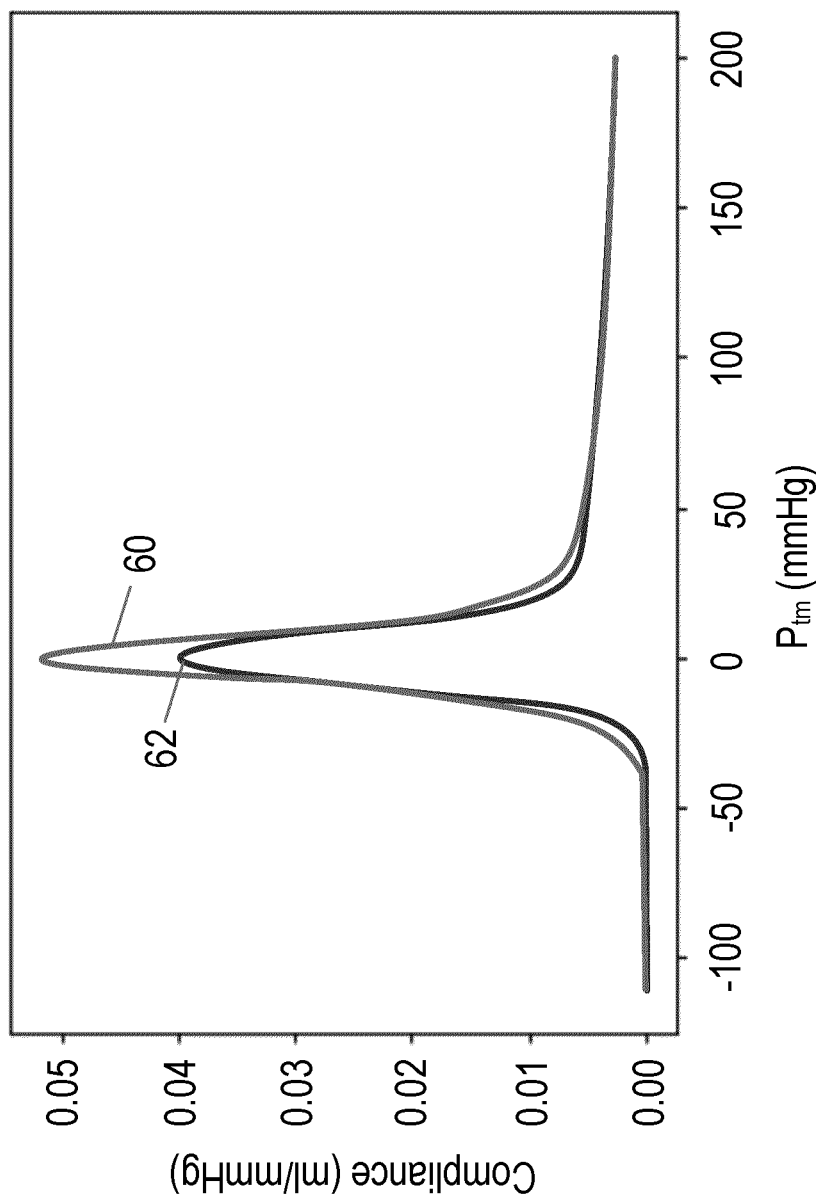
FIG. 6 is a graph illustrating a comparison between newly acquired arterial compliance values and arterial compliance measured at the time that a calibration procedure was performed.

In step 115 this further estimate of arterial compliance determined in step 113 can be compared to the baseline arterial compliance determined in step 105 to confirm whether or not the PAT change occurred due to an alteration in arterial compliance. As in steps 103 and 105, the new estimate of arterial compliance is based on an oscillometric signal obtained from the cuff pressure sensor 8 and a simultaneously acquired PAT-derived PWV over a range of arterial wall transmural pressures. The graph in FIG. 6 illustrates a comparison between newly acquired arterial compliance values (from step 113) for a range of transmural pressures (denoted P_tm) and arterial compliance measured at the time that a calibration procedure was performed. Line 60 in FIG. 6 represents the baseline arterial compliance values for a range of transmural pressures, and line 62 represents the newly acquired arterial compliance values for the range of transmural pressures. In some embodiments, the comparison in step 115 can suggest that PAT change occurred due to an alteration in arterial compliance if at any transmural pressure the newly acquired arterial compliance value differs by more than a threshold amount (e.g. 10% although other values can be used) from the arterial compliance measured at the time that the calibration procedure was performed. Alternatively the comparison in step 115 can involve determining an absolute difference or ratio of the measured arterial compliances, and optionally integrating the differences to obtain an aggregated value over a range of transmural pressures.

If the arterial compliance has changed from the baseline arterial compliance estimate, then current and future AWA CO measurements should be considered unreliable.

In some embodiments, the unreliability of the AWA CO measurements can be flagged or indicated to a care provider. For example a visual and/or audible indication of the unreliability can be provided by the apparatus 12 (e.g. a flag on a screen of a patient monitoring device). On observing the indication of unreliability, the care provider may initiate a further calibration procedure (e.g. thermodilution) in order to determine a new calibration CO measurement. In that case the method repeats from step 101.

In some embodiments, the indication of unreliability of the AWA CO measurements can be used to trigger or initiate a new calibration procedure (e.g. the thermodilution procedure). In that case, the method can return to step 101 and repeat to obtain a new calibration CO measurement and estimate of the baseline arterial compliance.

Figure 7:
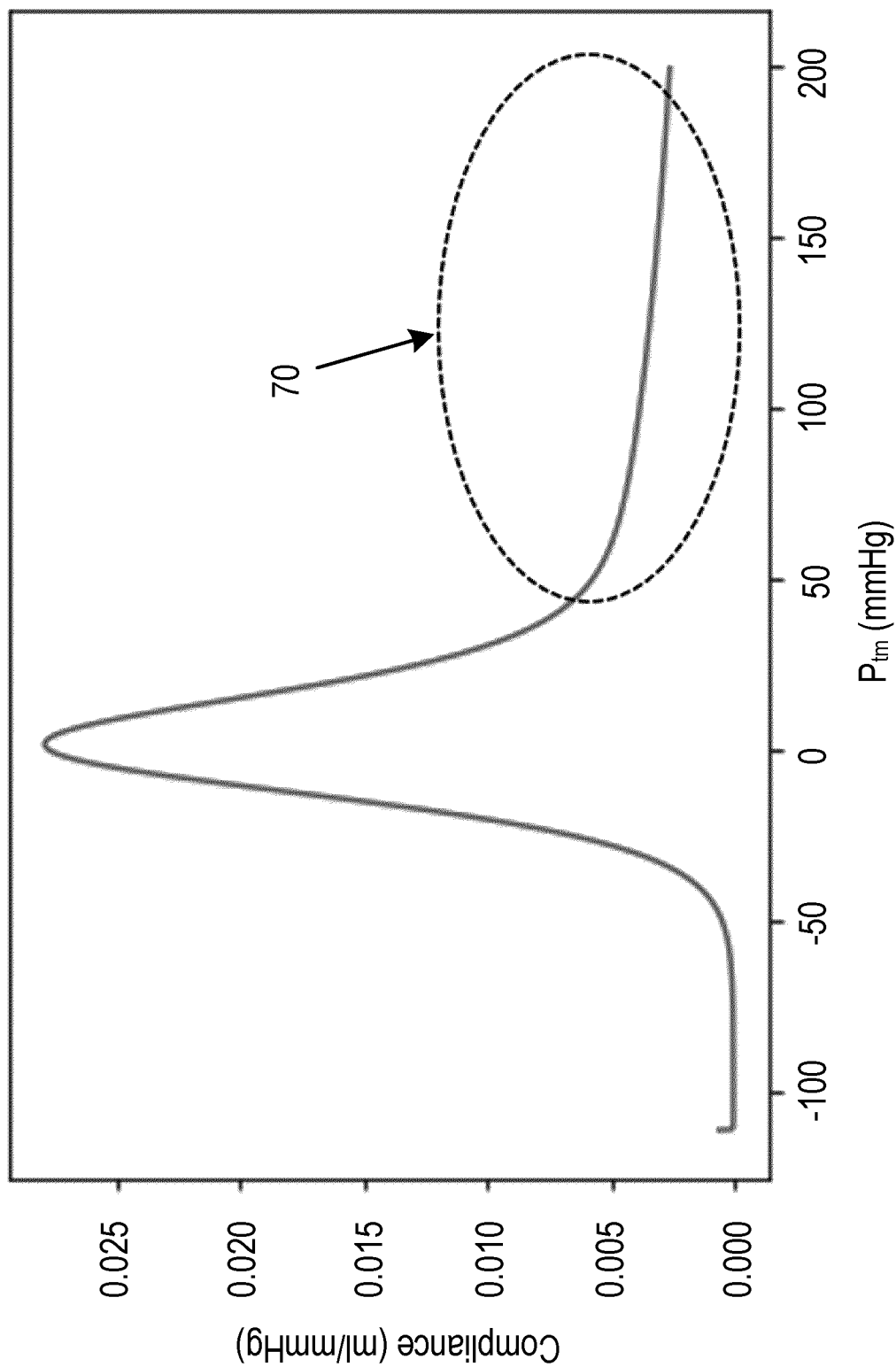
FIG. 7 is a graph illustrating arterial compliance against transmural pressure.

Alternatively (or in addition), and particularly in the case of smaller changes in the arterial compliance (e.g. changes that are less than a threshold), the newly acquired arterial compliance value can be used to determine adjustments to the value of C (the arterial compliance) used in the AWA model. FIG. 7 is a graph illustrating arterial compliance against transmural pressure, and provides an example of arterial compliance values that could be obtained at a brachial artery site. Since these values are only representative of properties of the artery segment under the cuff 4 (with the size of the artery segment being determined by the size of the cuff itself, e.g. the cuff can cover approximately 14 cm of artery) then this data can be used to scale the value of C that was previously obtained by thermodilution. The scaling of C can be a proportional increase or decrease, for example, to account for the entire length of the arterial tree, and/or taking into account other patient specific characteristics such as body-mass index (BMI) or body length (height).

FIG. 7 also shows how arterial compliance information can be obtained over a wider range of transmural pressure values to allow the derivation of a relationship between blood pressure and arterial compliance. This is useful for obtaining more accurate CO estimates in the event that BP changes, since the C parameter in Equation (1) is dependent on BP. The cuff 4 applies external pressure on the arm 36 and the transmural pressure over the arterial wall ($P_{tm}$) is defined as:

$$P_{tm} = P_{art} - P_{cuff} \qquad (2)$$

where $P_{art}$ is arterial pressure varying between systolic and diastolic values and $P_{cuff}$ is pressure inside the cuff 4. Therefore, a change in $P_{cuff}$ can alter $P_{tm}$ and "simulate" a change in blood pressure. This allows C to be inferred in this range, and values can be stored, e.g. in a look-up table.

FIG. 7 shows an example of arterial compliance values that could be measured over a gradual inflation of the cuff up to supra-systolic pressures. However, this complete inflation of the cuff is not necessary, since blood pressure is not likely to vary more than 20-40 mmHg in typical patient conditions in care settings. This is shown in FIG. 7 as the "operating region" 70. For this reason, the cuff 4 could be inflated only up to mean arterial pressure (for example), or perhaps less. Values of the systolic and diastolic pressures in this case can be obtained via the invasive arterial site 32.

Therefore, the method described above will enable more accurate CO estimations using AWA than currently available techniques. This is due to the arterial compliance being available for a range of pressures, whereas currently only a point calibration at the blood pressure at the time that the calibration CO measurement is obtained is taken into account. In particular, by obtaining arterial compliance values over a range of blood pressures, it is possible to adapt the arterial compliance parameter in the AWA CO inference process depending on the measured pressure. For example, using the AWA technique an unaltered (unprocessed) AP waveform is processed to estimate CO, e.g. at 100 mmHg mean arterial pressure, which causes a 100 mmHg mean transmural pressure across the arterial wall. With the cuff 4 the transmural pressure across the arterial wall can be changed. If the AP waveform is recorded when the cuff pressure is held at a plateau (e.g. the cuff pressure=20 mmHg, causing a mean transmural pressure of 80 mmHg) then a different waveform will be obtained. Subsequently, if the blood pressure decreases from 100 mmHg mean pressure to 80 mmHg mean pressure, then the AWA CO technique can be adjusted based on the CO measurement previously performed at 20 mmHg cuff pressure during calibration.

In a second specific embodiment, the reliability of AWA CO measurements for a subject 30 is estimated only using measurements of pressure oscillations in the cuff 4. That is, unlike the first embodiment above, neither of a PPG sensor 16 or ECG sensor 18 are present or used. In this second embodiment, steps 101 and 103 are performed as above, except that a PPG signal and an ECG signal are not obtained. In step 105, the baseline arterial compliance is estimated by analysing the cuff pressure signal obtained during the calibration procedure. Briefly, the acquired cuff pressure oscillations are translated into arm volume changes and then to quantified artery volume changes from which artery compliance is inferred. Those skilled in the art will be aware of various techniques for estimating the arterial compliance from the cuff pressure signal obtained during the calibration procedure. For example, a suitable technique is described in "A modelling framework for assessment of arterial compliance by fusion of oscillometry and pulse wave velocity information" by Bogatu, L. I., Turco, S., Mischi, M., Woerlee, P., Bouwman, A., Korsten, E. H. H. M., & Muehlsteff, J., Computer Methods and Programs in Biomedicine, 196, (2020). Other suitable techniques can be found in WO 2020/126576, and International (PCT) Patent Application no. PCT/EP2020/068331.

Steps 107 and 109 are omitted, and after the calibration procedure (step 101) the cuff pressure signal continues to be obtained, for example either continuously, or, preferably intermittently (since it requires the inflation of the cuff 4 which can be inconvenient for the subject 30). This generally corresponds to step 111, and the cuff pressure signal analysed in step 113 to estimate the arterial compliance. Step 115 compares the baseline estimate of arterial compliance to the newly determined estimate to determine if the AWA CO measurements are still reliable.

In a third specific embodiment, a potential change in arterial compliance since a calibration procedure was performed can be inferred analysing the morphology (e.g. shape) of the PPG signal from the PPG sensor 16. As in the first and second specific embodiments, the cuff pressure signal is obtained and used to estimate the arterial compliance.

In this third embodiment, steps 101 and 103 are performed as above, including obtaining a PPG signal during the calibration procedure. However, rather than determine PAT or PWV, the morphology of the PPG signal can be analysed to provide a baseline morphology (i.e. a morphology corresponding to when the calibration procedure was performed). Aspects of the morphology that can be considered include decomposition in to forward and reflected waves, or using higher order derivatives, from which Pulse Transit Time (PTT) can be derived. Other aspects include, on a beat-to-beat basis, the ratio of the amplitude of PPG to arterial pulse pressure ($PPG_{amp}/PP$, as relative vascular compliance) to total peripheral resistance (TPR) and Windkessel compliance ($C_{wk}$) obtained from the Modelflow CO algorithm (as described in "The photoplethysmographic amplitude to pulse pressure ratio can track sudden changes in vascular compliance and resistance during liver graft reperfusion" by Wook-Jong Kim et al., in Medicine (Baltimore), 2 Jun. 2017; 96(22):e7045.

In step 105, the baseline arterial compliance is estimated by analysing the cuff pressure signal obtained during the calibration procedure. This can be performed in a similar way to in the second specific embodiment above.

In this third embodiment, steps 107 and 109 comprise obtaining a PPG signal and analysing the morphology of the PPG signal to determine if the morphology has changed since the calibration procedure. If a change in morphology is identified in step 109, then steps 111 and 113 can be performed to re-estimate the arterial compliance. Step 115 compares the baseline estimate of arterial compliance to the newly determined estimate to determine if the AWA CO measurements are still reliable, as in the first specific embodiment.

It will be appreciated that the analysis of the PPG signal morphology can also be used in the first specific embodiment, alongside the estimation of the PAT and PWV.

Figure 8:
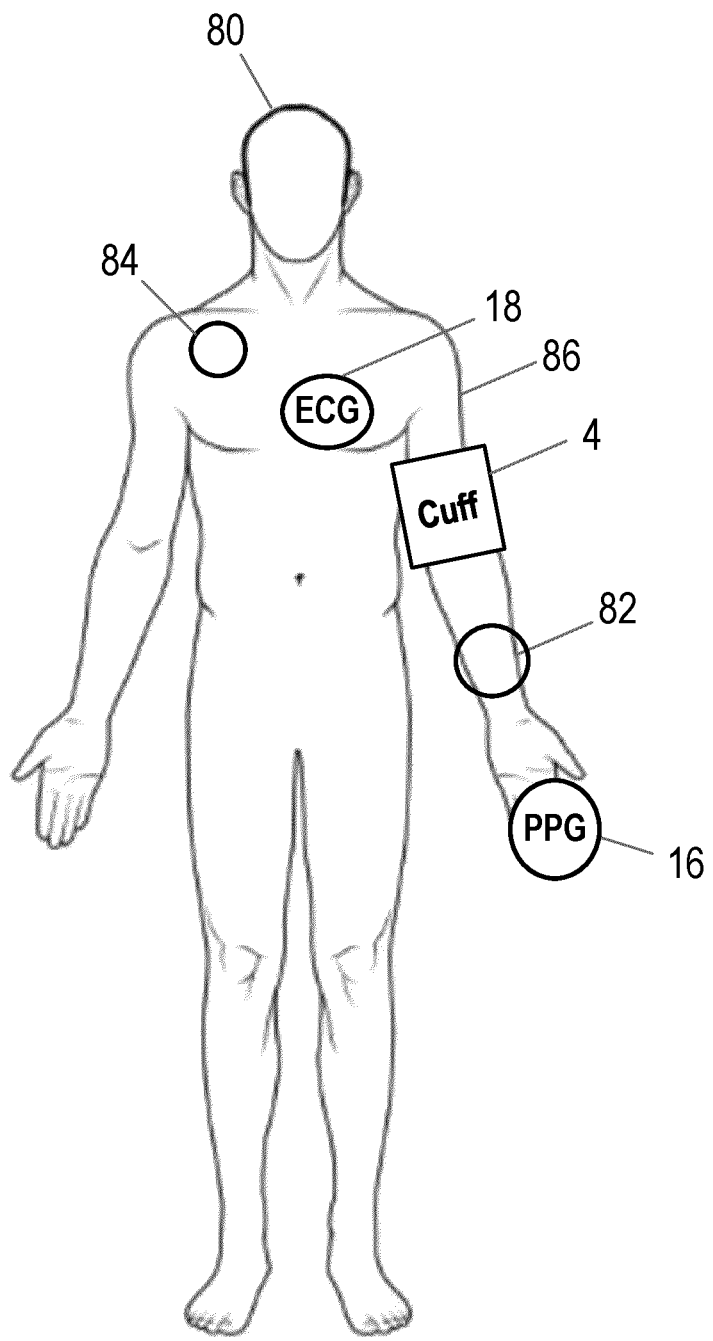
FIG. 8 is an illustration of an exemplary measurement setup on a subject according to an embodiment in which there is arterial invasive access on a same arm where a cuff is placed.

FIG. 8 illustrates an exemplary measurement setup on a subject according to a second exemplary set of embodiments. In this set of embodiments, the reliability of AWA CO measurements is estimated by taking into account arterial pressure measurements obtained invasively. This can improve the estimation of the arterial compliance. In these embodiments the arterial access site for the thermodilution measurement and the AP sensor 20 is required to be on the same limb (e.g. arm) as the cuff 4.

FIG. 8 shows a subject 80 for whom a thermodilution CO measurement is performed via invasive access to an arterial site 82 and a venous site 84. As noted, the arterial access site should be on the same limb as the cuff, and the arterial access site/AP sensor 20 should be distal with respect to the cuff 4. In FIG. 8 the arterial access site is shown to be at a radial artery access site 82 on the left arm 86 of the subject 80, with the cuff 4 on the upper arm, although a brachial artery access site could be used instead (provided that the cuff 4 is high enough up the arm). The venous access can be any central venous sites. In FIG. 8 the venous access site 84 is shown to be at an axillary vein access site 84. Temperature sensors will typically be present in each of the sites to enable the thermodilution measurement to be made. Although not shown in FIG. 8, the AP sensor 20 is typically located at the same arterial access site used for thermodilution (e.g. the arterial access site 82 in FIG. 8).

The cuff 4 is placed on the same arm as the arterial access site 82, and thus the cuff 4 is placed on the left arm 86 of the subject 80. FIG. 8 also shows PGG sensor 16 placed on the left hand (or on one or more fingers of the left hand) of the subject 80, and ECG sensor 18 is placed in the region of the heart of the subject 80 (in the typical way for ECG sensors). The PPG sensor 16 should be present on the same limb as the cuff 4. As noted below, in some embodiments the PPG sensor 16 and/or the ECG sensor 18 are not required.

In a first specific embodiment of the second set of embodiments, the reliability of AWA CO measurements for a subject 30 is estimated using measurements of pressure oscillations in the cuff 4, measurements of arterial pressure (AP) obtained by AP sensor 20, and one or both of a PPG signal from PPG sensor 16 and an ECG signal from ECG sensor 18. An exemplary method according to this embodiment is similar to that shown in FIG. 4. However, AP measurements are obtained by the AP sensor 20 during the calibration procedure (step 101), and in particular when the cuff 4 is inflated in step 103, and also when the cuff 4 is inflated in step 111.

Access to the arterial line at a brachial/radial site (e.g. site 82) can improve the accuracy of the arterial compliance estimation in steps 105 and 113. Having the AP signal allows consideration of full pressure and volume waveforms when estimating arterial compliance, rather than relying on oscillation amplitudes alone (i.e. from the cuff pressure signal). Therefore, steps 105 and 113 further take into account the AP measurements for the estimation of arterial compliance, and a more accurate arterial compliance estimation is achieved as the non-invasive measurements (the cuff pressure signal) is complemented by the invasive measurement (the AP signal).

The approach is based on the estimation of the arterial compliance via equation (3):

$$C_a(p_{tm}(t)) = \frac{dV_a(t)}{dP_a(t)} \quad (3)$$

Arterial compliance can be obtained if arterial volume $V_a$ and pressure waves $P_a$ are available. In OR and ICU environments arterial pressure waves $P_a$ are often acquired by means of invasive arterial lines. For reasons of redundancy, non-invasive cuff based oscillometric BP measurements are also used. Vessel wall oscillations are detected as pressure oscillations in the cuff. If cuff compliance is known (the translation from pressure to volume changes in the cuff), then information about arterial volume $V_a$ can be obtained. By appropriate processing of the signals in terms of synchronicity, arterial compliance can be derived by:

$$C_a = \frac{\frac{dV_a}{dt}}{\frac{dP_a}{dt}} \quad (4)$$

In a practical implementation the low-noise derivatives of the acquired and synchronized need to be calculated and divided."

In a second specific embodiment of the second set of embodiments, the simultaneous recording of AP measurements, an ECG signal and a PPG signal during inflation of the cuff 4 can be used to differentiate between arterial compliance changes that occur centrally versus those that occur peripherally. These types of arterial compliance changes are described in "Effects of vasoactive drugs on the relationship between ECG-pulse wave delay time and arterial blood pressure in ICU patients" by W. Zong, G. Moody and R. Mark, in *Computers in Cardiology* 1998, Vol. 25, and "Ageing and vascular ageing" by Jani, B, and C Rajkumar, Postgraduate medical journal vol. 82,968 (2006): 357-62.

Thus, in steps 105 and 113, the arterial compliance at the periphery can be estimated from measurements of ABP and PPG derived PAT, and the central arterial compliance can be estimated from measurements of PAT derived from ECG and ABP, and oscillometry (i.e. the cuff pressure signal). The differences in these estimated arterial compliances can be used to determine whether AWA CO measurements are reliable. For example, the reliability of the AWA CO measurements can be found by comparing peripheral arterial compliance (since peripheral arterial compliance is more prone to change), or by comparing the more central arterial compliance. Alternatively a baseline relationship between the peripheral arterial compliance and the central arterial compliance can be derived, and it can be checked that the same relationship holds for the subsequent measurement.

Figure 9:
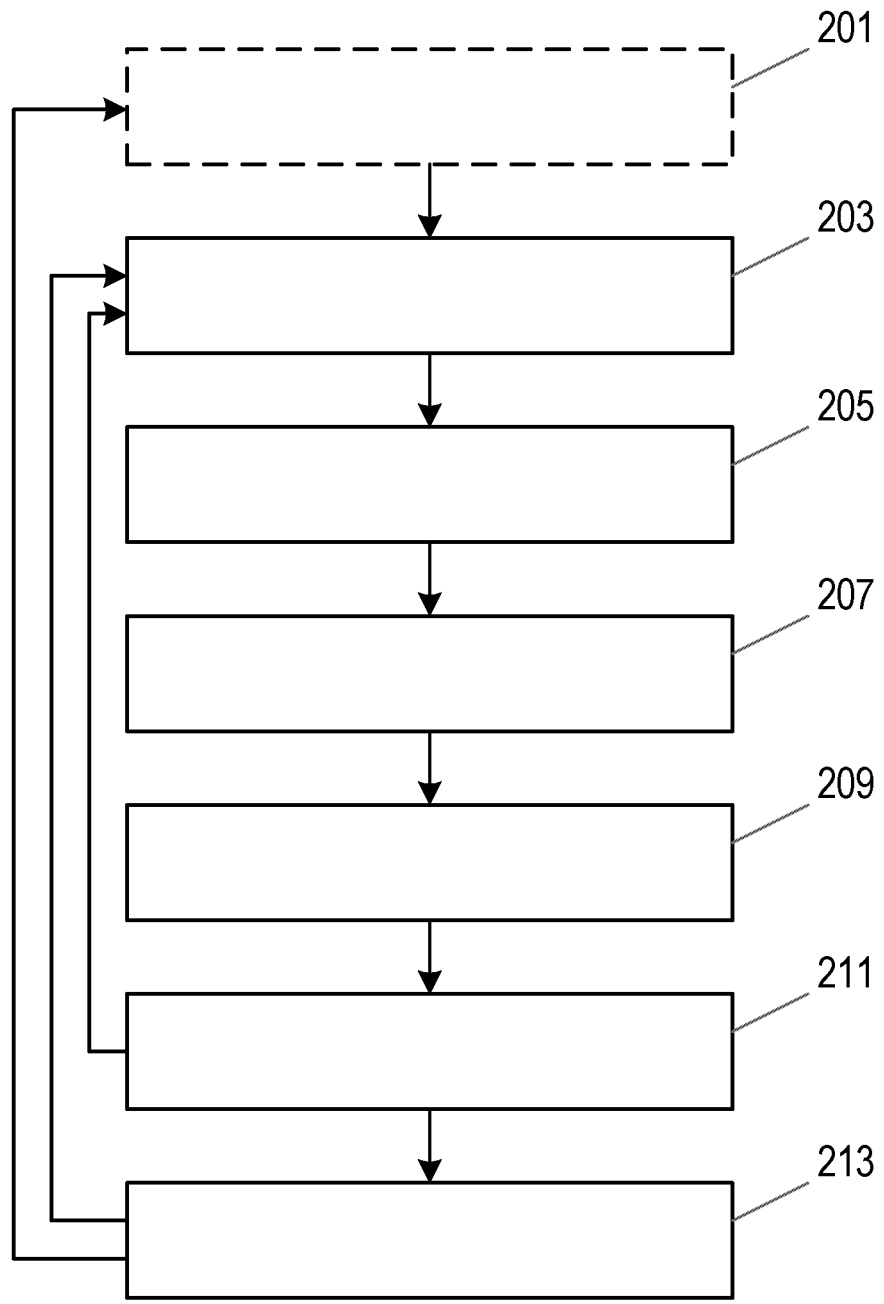
FIG. 9 is a flow chart illustrating a method of estimating the reliability of AWA CO measurements according to a general embodiment.

A general method according to the techniques described herein is shown in FIG. 9. One or more of the steps in FIG. 9 can be performed by the system 2, apparatus 12 and/or processing unit 22.

In step 203, inflation of a cuff 4 that is at a first location on a subject (e.g. around a limb, such as an arm) is initiated.

Next, in step 205, which occurs as the cuff 4 is being inflated, a cuff pressure signal is obtained that comprises measurements of pressure inside the cuff 4 during inflation. Steps 203 and 205 correspond generally to step 103 in the above specific embodiments.

In step 207 the cuff pressure signal is analysed to derive a relationship between oscillations in arterial volume beneath the cuff 4 and pressure in the arteries.

In step 209, an arterial compliance of the arteries is estimated for a range of cuff (transmural) pressures. The arterial compliance is estimated based on the relationship determined in step 207. Steps 207 and 209 are generally as described above with reference to step 105 of the above specific embodiments.

A first 'round' of steps 203-209 is performed during a first time period in which a calibration CO measurement is obtained for the subject using a thermodilution CO measurement technique. Thus, the AWA technique is calibrated using a thermodilution CO measurement obtained in the first time period. When steps 203-209 are performed when a calibration CO measurement is obtained, this 'round' can be referred to as a 'calibration round'. Optional step 201 (which is performed prior to or at the same time as step 203) represents the initiation of the thermodilution calibration procedure. Step 201 can generally correspond to step 101 of the above specific embodiments. The output of step 209 in this first round of steps 203-209 is referred to as a 'first arterial compliance', and, as noted, represents the arterial compliance of the arteries for a range of transmural pressures. Thus, the first time period is a time period in which the first arterial compliance is measured, and is a time period in which a calibration CO measurement is obtained and used to calibrate the AWA technique. Therefore, the first arterial compliance is measured at generally the same time that the CO is measured directly, e.g. using thermodilution.

In embodiments in which the method is implemented by the system 2, apparatus 12 and/or processing unit 22, the processing unit 22 can be manually controlled to perform the first round of steps 203-209 when a thermodilution CO measurement is being obtained. Alternatively, the processing unit 22 can be automatically controlled (e.g. in response to receiving a control signal from a thermodilution CO measurement apparatus) to perform the first round of steps 203-209 when a thermodilution CO measurement is being obtained. Alternatively, the processing unit 22 can be automatically controlled to perform the first round of steps 203-209 at a desired time (e.g. according to a schedule) and initiate a thermodilution CO measurement. In any of these ways, the first arterial compliance will be measured during the time period in which the thermodilution CO measurement is obtained.

Subsequently, in step 211, in a second time period that is after the first time period, a second round of steps 203-209 is triggered in which steps 203-209 are repeated to provide a further estimate of the arterial compliance of the arteries. This further estimate is referred to as a 'second arterial compliance'. As noted, the 'second arterial compliance' represents the arterial compliance of the arteries for a range of transmural pressures. The repetition of steps 203-209 triggered by step 211 can generally correspond to steps 111 and 113 of the above specific embodiments.

Once the repetition of steps 203-209 triggered by step 211 is complete, the method passes to step 213. In step 213, the first arterial compliance and the second arterial compliance are compared, and the result of the comparison (e.g. a difference) between the first arterial compliance and the second arterial compliance is used to determine a reliability of CO measurements obtained using the AWA technique.

In some embodiments, if the AWA CO measurements are considered to be reliable, then the method can return, at some subsequent third time period, to step 203, and a further round of steps 203-209 is performed. If the AWA CO measurements are considered to be unreliable, then a new calibration CO measurement may be required. In that case, the method can return to step 201 in order to automatically initiate a new thermodilution CO measurement and calibration of the AWA model. Alternatively, the method can further comprise indicating the unreliability of the AWA CO measurements to a user of the apparatus 12 or system 2 (such as a care provider via a display screen or other user interface component of the apparatus 12 or system 2), and the care provider can manually initiate the new thermodilution measurement in step 201. As a further alternative, if the AWA CO measurements are considered to be unreliable, then an adjustment to the value of the arterial compliance parameter (C) in the AWA model can be determined instead of obtaining a new calibration CO measurement. The adjustment can be determined as a function of the second arterial compliance, and/or as a function of the difference between the first arterial compliance and the second arterial compliance. For example, the newly measured arterial compliance can be input to the Windkessel model to output a more accurate estimation of CO. Alternatively the output CO can be scaled with respect to a ratio of the arterial compliance at calibration (compliance 1) and the current arterial compliance (compliance 2). In embodiments where an adjustment to C in the AWA model is determined, the method can return to step 203 in some subsequent time period.

In some embodiments, step 213 can comprise comparing the result of the comparison to a threshold. The result of the comparison may be the difference, the magnitude of the difference, or a fractional or percentage change in the arterial compliance. If the difference, magnitude of the difference, or the fractional or percentage change (as appropriate) is above a threshold, then the AWA CO measurements can be considered unreliable, and reliable otherwise. In the case of a fractional or percentage change, a threshold of 10% may be suitable. In the case of a difference or magnitude of the difference, a suitable threshold can be set at around 10% of a typical arterial compliance value.

In some embodiments, the method performed by the system 2 or the apparatus 12 can further comprise obtaining one or more AWA CO measurements. This step can be performed continuously, periodically or when a CO measurement is required. This step comprises obtaining an arterial pressure (AP) signal that represents the AP over time, and processing the AP signal using the AWA model to determine the cardiac output.

In some embodiments, where the AP signal used by the AWA model is obtained from the same limb that the cuff 4 is placed around, the AP signal can be obtained during steps 203 and 205, and step 207 can comprise analysing the first cuff pressure signal and the AP signal to derive the relationship between oscillations in arterial volume beneath the cuff 4 and pressure in the arteries.

In some embodiments, one or both of a PPG signal and an ECG signal are obtained when steps 203 and 205 are performed. This or these signals are analysed in step 207 to determine a PAT and/or PWV for the subject, and the PAT and/or PWV is used in step 209, along with the relationship determined in step 207, to estimate the first arterial compliance.

In further embodiments, when the PAT is determined during a calibration round of steps 203-209, once the calibration round is complete, the PPG signal and/or ECG signal can continue to be obtained and analysed to determine the PAT for the subject. This or these PAT values can be compared to the PAT value determined during the calibration round, and the result of the comparison of the PAT values can be used to determine whether step 211 should be performed and a second arterial compliance estimated. In particular, as noted above, a change in PAT can (but not necessarily) indicate a change in arterial compliance, and thus monitoring changes in PAT can provide an indication of whether arterial compliance may have changed. Therefore, if the result of the comparison indicates that the PAT has changed by a sufficient amount (e.g. 10%, although other values can be used), step 211 can be performed. If the result of the comparison indicates that the PAT has not changed by a sufficient amount, then the CO measurements obtained using the AWA technique can continue to be considered as reliable.

In embodiments where the PPG signal and ECG signal are not available (e.g. because the system 2 does not include the PPG sensor 16 and the ECG sensor 18), then in step 209 the first arterial compliance can be estimated based only on the first cuff pressure signal. In these embodiments, step (b) can be repeated intermittently or periodically, i.e. the second time period in step (b) is a predefined time after the first time period. In some embodiments, step (b) can be performed every X minutes, where X can be a value in the range of 5 to 60.

In embodiments where a PPG signal is available, a change in arterial compliance can be inferred from changes in PPG signal morphologies. Therefore, in some embodiments a PPG signal is obtained when steps 203 and 205 are performed and the PPG signal is analysed to determine a first PPG morphology. After step 209, a further PPG signal for the subject is obtained, and this further PPG signal is analysed to determine a second PPG morphology. A comparison of the second PPG morphology and the first PPG morphology is used to determine whether to perform step 211 based on the result of the comparison of the second PPG morphology to the first PPG morphology.

Therefore, there is provided a method, apparatus and system for estimating the reliability of CO measurements obtained using an AWA technique.

It will be appreciated that the techniques described herein can be implemented by computer programs, particularly computer programs on or in a carrier. The program may be in the form of a source code, an object code, a code intermediate source and an object code such as in a partially compiled form, or in any other form suitable for use in the implementation of the methods described herein. It will also be appreciated that such a program may have many different architectural designs. For example, a program code implementing the functionality of the method, apparatus or system described herein may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at runtime. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the apparatus, systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of estimating a reliability of cardiac output; (CO); measurements for a subject obtained using an arterial waveform analysis; (AWA), technique, wherein the AWA technique is calibrated using CO measurements obtained using a thermodilution CO measurement technique, the method comprising:
   (a) during a first time period in which the AWA technique is calibrated using a first CO measurement obtained using the thermodilution CO measurement technique:
      (i) initiating inflation of a cuff that is at a first location on the subject;
      (ii) obtaining a first cuff pressure signal comprising measurements of pressure inside the cuff during inflation;
      (iii) analysing the first cuff pressure signal to derive a relationship between oscillations in arterial volume beneath the cuff and pressure in the arteries; and
      (iv) estimating a first arterial compliance of arteries for a range of cuff pressures based on the determined relationship;
   (b) during a second time period that is after the first time period, repeating steps (i)-(iv) to estimate a second arterial compliance of the arteries; and
   (c) using a result of a comparison of the first arterial compliance and the second arterial compliance to determine a reliability of CO measurements obtained using the AWA technique during the second time period.

2. The method as claimed in claim 1, wherein if the CO measurements obtained using the AWA technique during the second time period are determined to be reliable, the method further comprises:
   (d) during a third time period that is after the second time period repeating steps (i)-(iv) to estimate a third arterial compliance of the arteries; and
   (e) repeating step (c) using the second arterial compliance and the third arterial compliance.

3. The method as claimed in claim 1, wherein if the CO measurements obtained using the AWA technique during the second time period are determined to be unreliable, the method further comprises one or more of:
   initiating the thermodilution CO measurement technique to obtain a second CO measurement and calibrating the AWA technique using the second CO measurement;
   indicating the unreliability of the measurements obtained using the AWA technique to a user; and
   determining an adjustment to a value of an arterial compliance parameter used in the AWA technique based on the result of the comparison.

4. The method as claimed in claim 1, wherein the method further comprises:
   obtaining a photoplethysmogram, (PPG), signal and/or an electrocardiogram, (ECG), signal for the subject when steps (i) and (ii) are performed; and
   analysing the PPG signal and/or the ECG signal to determine a first pulse arrival time, (PAT), and/or a first pulse wave velocity, (PWV), for the subject;
   wherein step (iv) comprises estimating the first arterial compliance of the arteries for the range of cuff pressures based on the determined relationship and the first PAT and/or the first PWV.

5. The method as claimed in claim 4, wherein the method further comprises:
- after step (iv), obtaining a further PPG signal and/or a further ECG signal for the subject;
- analysing the further PPG signal and/or the further ECG signal to determine a second PAT for the subject;
- comparing the second PAT to the first PAT; and
- determining whether to perform step (b) based on the result of the comparison of the second PAT to the first PAT.

6. The method as claimed in claim 1, wherein the second time period is a predefined time after the first time period.

7. The method as claimed in claim 1, wherein the method further comprises:
- obtaining a photoplethysmogram; (PPG); signal for the subject when steps (i) and (ii) are performed;
- analysing the PPG signal to determine a first PPG morphology;
- after step (iv), obtaining a further PPG signal for the subject;
- analysing the further PPG signal to determine a second PPG morphology;
- comparing the second PPG morphology to the first PPG morphology; and
- determining whether to perform step (b) based on the result of the comparison of the second PPG morphology to the first PPG morphology.

8. The method as claimed in claim 1, wherein the method further comprises:
- obtaining an arterial pressure; (AP); signal for the subject representing the AP of the subject when steps (i) and (ii) are performed;
- wherein step (iii) comprises analysing the first cuff pressure signal and the AP signal to derive the relationship between oscillations in arterial volume beneath the cuff and pressure in the arteries.

9. An apparatus for estimating a reliability of cardiac output; (CO); measurements for a subject obtained using an arterial waveform analysis; (AWA); technique, wherein the AWA technique is calibrated using CO measurements obtained using a thermodilution CO measurement technique, the apparatus comprising a processor configured to:
- (a) during a first time period in which the AWA technique is calibrated using a first CO measurement obtained using the thermodilution CO measurement technique:
  - (i) initiate inflation of a cuff that is at a first location on the subject;
  - (ii) obtain a first cuff pressure signal comprising measurements of pressure inside the cuff during inflation;
  - (iii) analyse the first cuff pressure signal to derive a relationship between oscillations in arterial volume beneath the cuff and pressure in arteries; and
  - (iv) estimate a first arterial compliance of the arteries for a range of cuff pressures based on the determined relationship;
- (b) during a second time period that is after the first time period, repeat functions (i)-(iv) to estimate a second arterial compliance of the arteries; and
- (c) use a result of a comparison of the first arterial compliance and the second arterial compliance to determine a reliability of CO measurements obtained using the AWA technique during the second time period.

10. The apparatus as claimed in claim 9, wherein the processor is further configured to:
- obtain a photoplethysmogram, (PPG), signal and/or an electrocardiogram, (ECG), signal for the subject when functions (i) and (ii) are performed; and
- analyse the PPG signal and/or the ECG signal to determine a first pulse arrival time, (PAT), and/or a first pulse wave velocity, (PWV), for the subject;
- wherein function (iv) comprises estimating the first arterial compliance of the arteries for the range of cuff pressures based on the determined relationship and the first PAT and/or the first PWV.

11. The apparatus as claimed in claim 10, wherein the processor is further configured to:
- after function (iv), obtain a further PPG signal and/or a further ECG signal for the subject;
- analyse the further PPG signal and/or the further ECG signal to determine a second PAT for the subject;
- compare the second PAT to the first PAT; and
- determine whether to perform function (b) based on the result of the comparison of the second PAT to the first PAT.

12. The apparatus as claimed in claim 9, wherein the second time period is a predefined time after the first time period.

13. The apparatus as claimed in claim 9, wherein the processor is further configured to:
- obtain a photoplethysmogram, PPG, signal for the subject when functions (i) and (ii) are performed;
- analyse the PPG signal to determine a first PPG morphology;
- after function (iv), obtain a further PPG signal for the subject;
- analyse the further PPG signal to determine a second PPG morphology;
- compare the second PPG morphology to the first PPG morphology; and
- determine whether to perform function (b) based on the result of the comparison of the second PPG morphology to the first PPG morphology.

14. The apparatus as claimed in claim 9, wherein the processor is further configured to:
- obtain an arterial pressure, (AP), signal for the subject representing the AP of the subject when functions (i) and (ii) are performed;
- wherein function (iii) comprises analysing the first cuff pressure signal and the AP signal to derive the relationship between oscillations in arterial volume beneath the cuff and pressure in the arteries.

15. A computer program product comprising a non-transitory computer readable medium having computer readable code embodied therein, the computer readable code being configured such that, on execution by a suitable computer or processor, the computer or processor is caused to perform the method of claim 1.

* * * * *